(12) United States Patent
Tsai et al.

(10) Patent No.: US 9,395,315 B2
(45) Date of Patent: Jul. 19, 2016

(54) LENS MODULE TESTING DEVICE

(71) Applicant: HON HAI PRECISION INDUSTRY CO., LTD., New Taipei (TW)

(72) Inventors: Meng-Yu Tsai, New Taipei (TW); Yu-Han Chen, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 799 days.

(21) Appl. No.: 13/779,759

(22) Filed: Feb. 28, 2013

(65) Prior Publication Data

US 2014/0015518 A1 Jan. 16, 2014

(30) Foreign Application Priority Data

Jul. 10, 2012 (TW) .................................. 101124707

(51) Int. Cl.
*G01R 31/00* (2006.01)
*G01N 27/00* (2006.01)
*G01M 11/02* (2006.01)

(52) U.S. Cl.
CPC ........... *G01N 27/00* (2013.01); *G01M 11/0214* (2013.01)

(58) Field of Classification Search
CPC ........... G01R 31/2874; G01R 31/2886; G01R 31/2891; G01R 31/2862; G01R 31/2831; G01R 33/34046; G01R 33/3415; G01R 33/385; G01R 33/341; G01R 33/34007; G01R 33/307; G01R 33/30; G01R 33/34053; G01R 33/34092; G01R 33/302

USPC .................................. 324/318, 321, 383, 537
See application file for complete search history.

(56) References Cited

U.S. PATENT DOCUMENTS

| | | | | |
|---|---|---|---|---|
| 5,444,520 A | * | 8/1995 | Murano | ................... B41J 2/465 347/244 |
| 7,813,043 B2 | * | 10/2010 | Lusinchi | .............. G02B 13/001 359/619 |
| 7,943,002 B2 | * | 5/2011 | Lu | ........................... B65B 13/00 156/228 |
| 2010/0039713 A1 | * | 2/2010 | Lusinchi | .............. G02B 13/001 359/819 |
| 2011/0103051 A1 | * | 5/2011 | Wilcox | ................... F21S 2/005 362/235 |
| 2014/0027807 A1 | * | 1/2014 | Tasaki | ..................... H01L 33/58 257/98 |

\* cited by examiner

*Primary Examiner* — Tung X Nguyen
*Assistant Examiner* — Thang Le
(74) *Attorney, Agent, or Firm* — ScienBiziP, P.C.

(57) ABSTRACT

A device for testing a multiplicity of lens modules includes a base, a circuit board, a connection member, and a support assembly. The base includes a support surface. The support surface includes a loading area and a slide area. The circuit board is positioned on the base in the loading area. The circuit board includes a number of signal input interfaces. The connection element includes a shell and a number of elastic and flexible metal elements. Each metal element connects to the number of signal input interfaces. The support assembly supports the lens modules, and can slide in the slide area to bring the metal elements into electrical contact with the lens modules.

12 Claims, 4 Drawing Sheets

LENS MODULE TESTING DEVICE

BACKGROUND

1. Technical Field

The present disclosure relates to testing devices, and particularly to a lens module testing device.

2. Description of Related Art

Lens modules undergo various tests to ensure that standards of quality have been met. These tests are typically carried out manually. For example, the electronic devices in which a lens module has already been installed may be manually connected to testing machines and disconnected after the completion of testing. The manual requirement of such testing procedures is time-consuming and inefficient.

Therefore, it is desirable to provide a lens module testing device which can overcome the above-mentioned limitations.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure.

DETAILED DESCRIPTION

Figure 1:
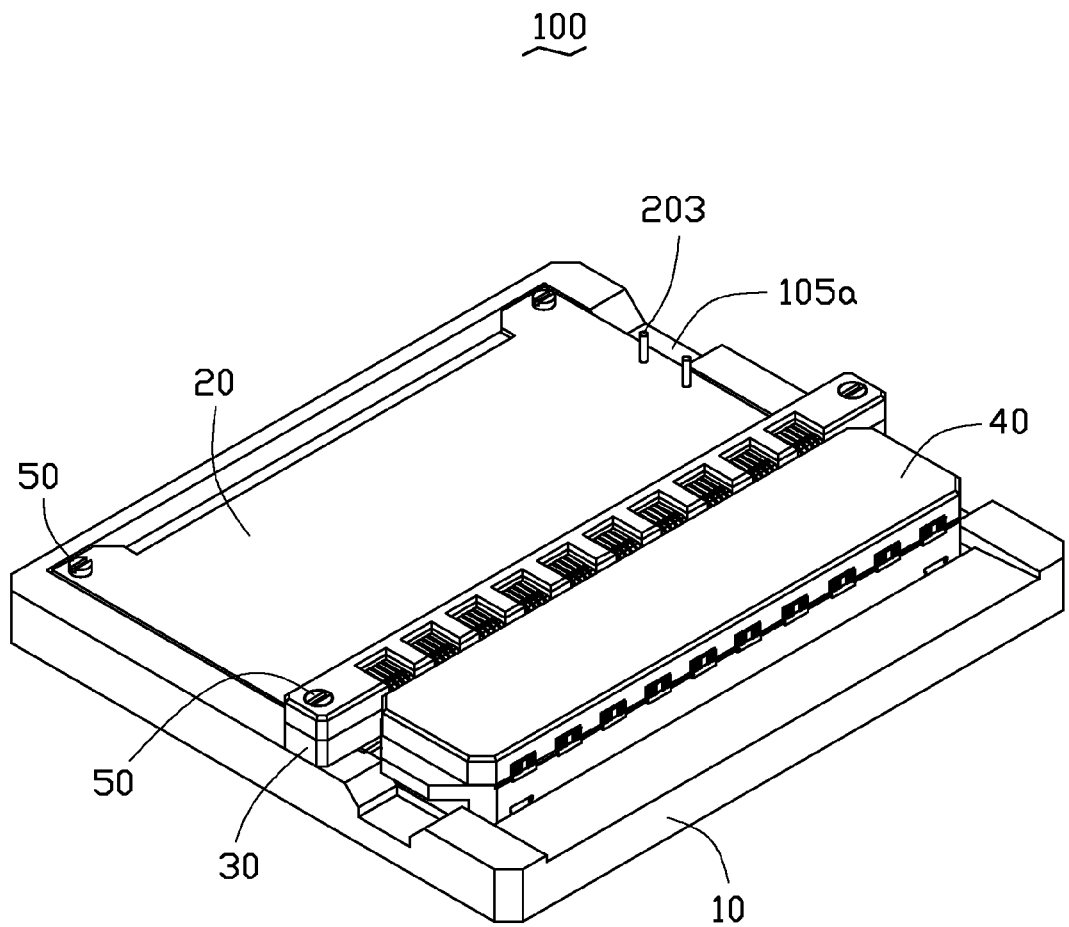
FIG. 1 is an assembled, isometric view of a lens module testing device which includes a connection member, according to an exemplary embodiment.
Figure 2:
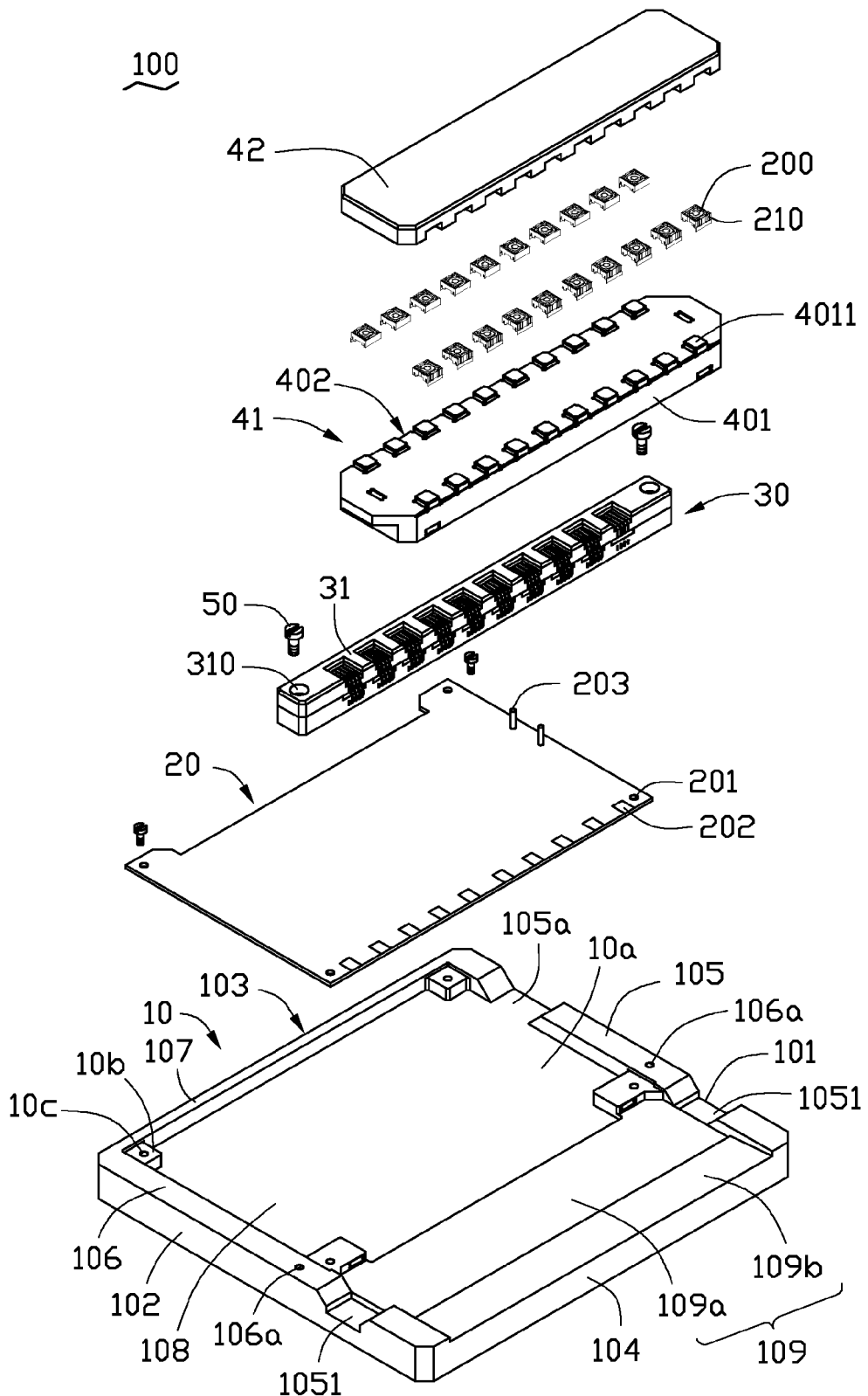
FIG. 2 is an exploded, isometric view of the lens module testing device of FIG. 1.
Figure 3:
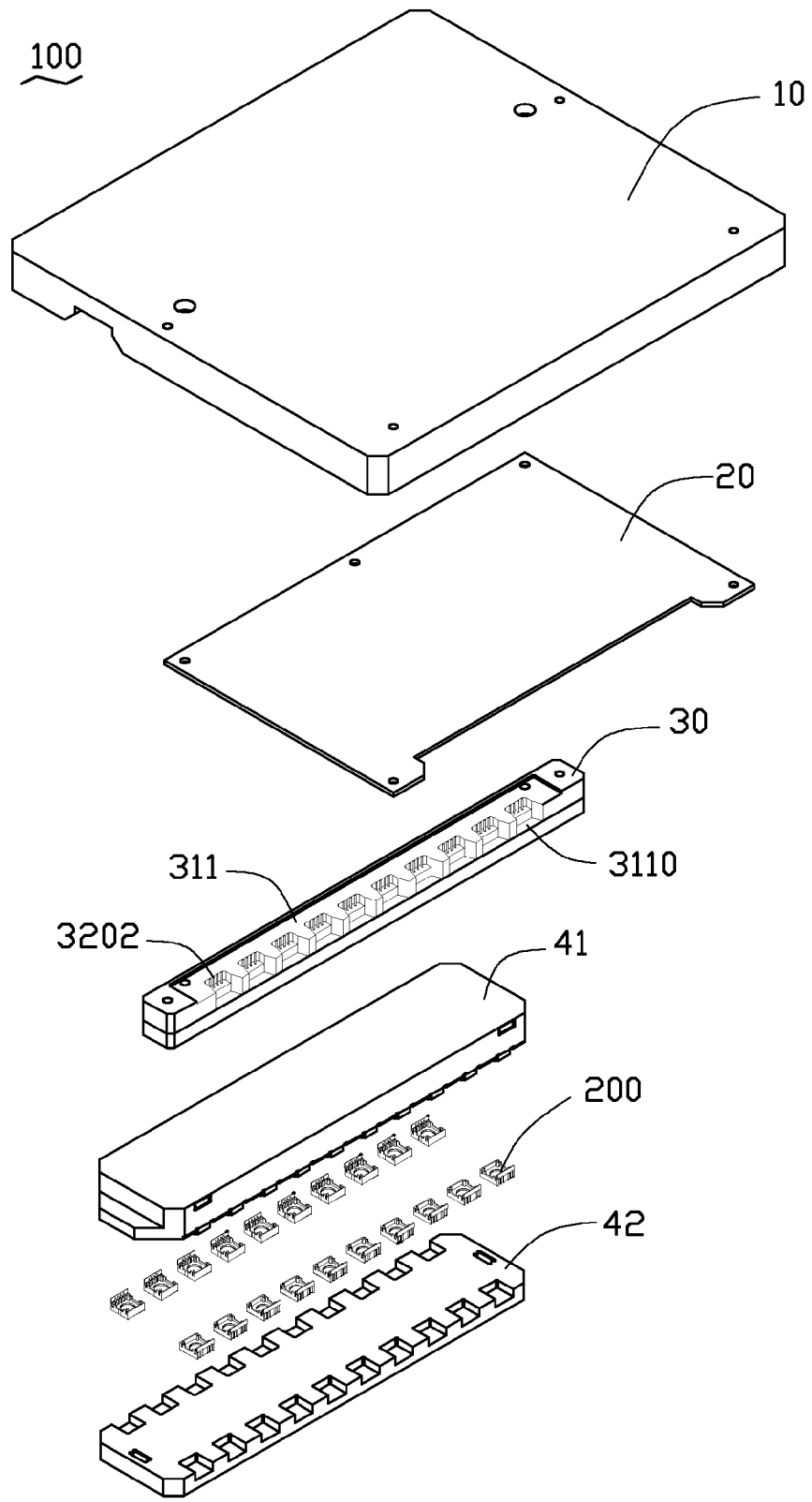
FIG. 3 is similar to FIG. 2, but viewed from another angle.

FIGS. 1-3 show a lens module testing device 100, according to an embodiment. The lens module testing device 100 is configured to test electrical properties of a number of lens modules 200. Each of the lens modules 200 includes a number of electrical contacts 210.

The lens module testing device 100 includes a base 10, a circuit board 20, a connection member 30 and a support assembly 40. The connection member 30 is positioned on the base 10 and electrically connects to the circuit board 20. The support assembly 40 is detachably positioned on the connection assembly 30, and is configured to support the number of lens modules 200.

The base 10 includes a support surface 10a. In the embodiment, the support surface 10a is substantially rectangular, and includes a first side surface 101, a second side surface 102 facing away from the first side surface 101, a third side surface 103, and a fourth side surface 104 facing away from the third side surface 103. The first side surface 101 is substantially parallel with the second side surface 102. The third side surface 103 is substantially parallel with the fourth side surface 104. Both the first side surface 101 and the second side surface 102 are substantially perpendicular to the third side surface 103 and the fourth side surface 104.

A first flange 105 perpendicularly extends upward from the first side surface 101. A second flange 106 perpendicularly extends upward from the second side surface 102. A third flange 107 perpendicularly extends upward from the third side surface 103. The first flange 105, the second flange 106 and the third flange 107 have essentially identical height in a direction perpendicular to the support surface 10a.

The support surface 10a includes a loading area 108 and a slide area 109. In the embodiment, the loading area 108 is also rectangular. Four locating blocks 10b perpendicularly extend upward from a joint of the first flange 105 and the third flange 107, from a joint of the second flange 106 and the third flange 107, from a joint of the first flange 105 and the slide area 109, and from a joint of the second flange 106 and the slide area 109. The four locating blocks 10b have essentially identical height. Each of the locating blocks 10b defines a first threaded hole 10c. The first flange 105 and the second flange 106 each define a second threaded hole 106a.

The slide area 109 includes a first slide area 109a adjacent to the loading area 108, and a second slide area 109b. The second slide area 109b is away from the loading area 108 and adjacent to the fourth side surface 104. A height of the second slide area 109b gradually reduces along a direction from the fourth side surface 104 toward the first slide area 109a, therefore, the second slide area 109b is a slope relative to the first sliding area 109a.

In the embodiment, the circuit board 20 is a printed circuit board (PCB). The size and the shape of the circuit board 20 correspond to the size and the shape of the loading area 108. The circuit board 20 defines four through holes 201, at the four corners of the circuit board 20. Each through hole 201 spatially corresponds to one of the first threaded holes 10c of the locating block 10b. In assembly, the circuit board 20 is supported on the four locating blocks 10b, with each of the through holes 201 aligning with a first threaded hole 10c, then four bolts 50 are run through the four through holes 10c to threadedly engage with the four first threaded holes 10c. The circuit board 20 also includes a number of signal input interfaces 202 positioned on a side surface of the circuit board 20, and two signal output interface 203 close to the first side surface 101.

The first flange 105 defines a first opening 105a communicating with the loading area 108. In disassembly, the first opening 105a allows convenient removal of the circuit board 20 from the locating blocks 10b.

Figure 4:
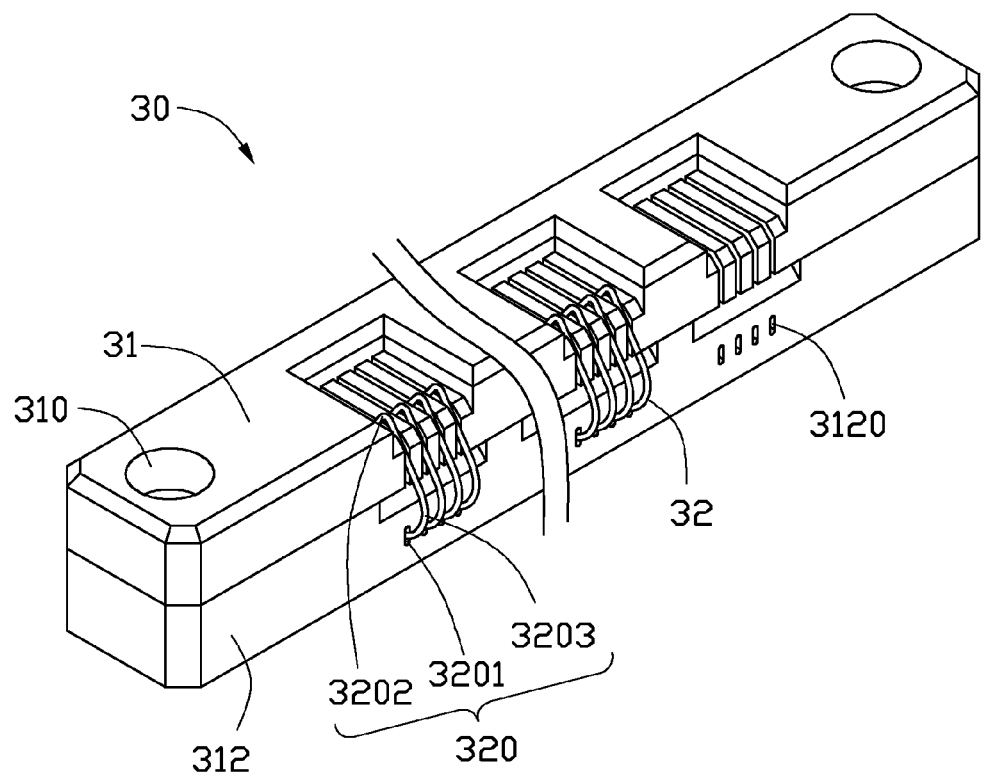
FIG. 4 is an assembled, isometric view of the connection member of FIG. 2.

Referring to FIG. 4, the connection assembly 30 includes a shell 31 and a number of elastic metal elements 32. The shell 31 defines two locating through holes 310 corresponding to the two second threaded holes 106a. In assembly, the connection assembly 30 is supported on the first flange 105 and the second flange 106, with each of the second threaded holes 106a aligning with a locating through hole 310, then two bolts 50 are run through the two locating through hole 310 to threadedly engage with the second threaded holes 106a.

The shell 31 includes a bottom surface 311 and a side surface 312 close to the slide area 109. The bottom surface 311 touches the first flange 105 and the second flange 106. The shell 31 defines a number of cavities 3110 in the bottom surface 311. The shell 31 also defines a number of fixing holes 3120 in the side surface 312.

Each of the elastic metal elements 32 includes a number of metal strips 320. Each of the metal strips 320 includes a first connection end 3201, a second connection end 3201 and an elastic portion 3203. Each of the first connection ends 3201 is received in one of the fixing holes 3120. Each of the second connection ends 3202 is received in one of the cavities 3110 (see FIG. 3). Each of the elastic portions 3203 can flex and bend outward from the shell 30 because the elastic portions 3203 have elasticity.

In the embodiment, a total height of the locating blocks 10b and the circuit board 20 is substantially equal to a height of the first flange 105, the second flange 106, the third flange 107 or the fourth flange 108, along a direction perpendicular to the support surface 10a of the base 10. Therefore, when assembling the connection assembly 30 on the first flange 105 and the second flange 106, each of the second connection ends 3202 of the metal strips 320 make contact with the signal input interfaces 202, to electrically connect the metal strips 320 to the circuit board 20.

The support assembly 40 includes a support substrate 41 and a cover 42 on the support substrate 41. The support assembly 40 is slidably positioned on the slide area 109. The support substrate 41 includes a first side wall 401 and a second side wall 402 facing away from the first side wall 401. Each of the first side wall 401 and the second side wall 402 form a number of fixed seats 4011 for loading a number of lens modules 200.

In the embodiment, each of the first flange 105 and the second flange 106 define a second opening 1051. Both of the two second openings 1051 communicate with the slide area 109. In disassembly, the two second openings 1051 allow convenient removal of the support assembly 40 from the base 10.

In use, the support assembly 40 slides on the slide area 109 towards the connection assembly 30 until the electrical contacts 210 of the lens modules 200 which are loaded on the fixed seats 4011 of the first side wall 401 make contact with the elastic portions 3203 of the metal strips 320. In this way, the lens modules 200 have an electrical connection with the circuit board 20, to test electrical properties of the lens modules 200. Then the support assembly 40 can be flipped and the above steps repeated, to bring the electrical contacts 210 of the lens modules 200 loaded on the fixed seats 4011 of the second side wall 402 into electrical contact with the elastic portions 3203 of the metal strips 320.

It will be understood that the above particular embodiments are shown and described by way of illustration only. The principles and the features of the present disclosure may be employed in various and numerous embodiment thereof without departing from the scope of the disclosure as claimed. The above-described embodiments illustrate the possible scope of the disclosure but do not restrict the scope of the disclosure.

What is claimed is:

1. A lens module testing device for testing electrical properties of a plurality of lens modules, each of the lens modules comprising a plurality of electrical contacts, the lens module testing device comprising:
a base comprising a support surface, the support surface comprising a loading area and a slide area;
a circuit board positioned on the base in the loading area, the circuit board comprising a plurality of signal input interfaces;
a connection assembly comprising a shell and a plurality of elastic metal elements, the connection assembly supported on the base, the shell comprising a bottom surface and a side surface close to the slide area, the shell defining a plurality of cavities in the bottom surface and a plurality of fixing holes in the side surface, each of the elastic metal elements comprising a plurality of metal strips, each of the metal strips comprising a first connection end, a second connection end and an elastic portion, the elastic portion connected between the first connection end and the second connection end, each of the first connection ends received in a respective one of the fixing holes, each of the second connection ends received in a respective one of the cavities, each of the elastic portions bending outward from the shell, the second connection ends touching the signal input interfaces; and
a support assembly configured to support the plurality of lens modules, the support assembly being capable of sliding in the slide area to make each of the elastic portions be electrically connected to a respective one of electrical contacts of one of the lens modules.

2. The lens module testing device of claim 1, wherein the support surface is substantially rectangular, and comprises a first side surface, a second side surface facing away from the first side surface, a third side surface and a fourth side surface facing away from the third side surface, the base comprises a first flange perpendicularly extending upward from the first side surface, a second flange perpendicularly extending upward from the second side surface, and a third flange perpendicularly extending upward from the third side surface, and the connection assembly is supported by the first and second flanges.

3. The lens module testing device of claim 2, wherein the first flange, the second flange and the third flange have an essentially identical height in a direction perpendicular to the supporting surface.

4. The lens module testing device of claim 3, wherein the base comprises four locating blocks, the four locating blocks perpendicularly extend upward from a joint of the first flange and the third flange, from a joint of the second flange and the third flange, from a joint of the first flange and the slide area, and from a joint of the second flange and the slide area, and the circuit board is supported by the four locating blocks and positioned beneath the connection assembly.

5. The lens module testing device of claim 4, wherein the four locating blocks have an essentially identical height.

6. The lens module testing device of claim 4, wherein the first flange defines a first opening communicating with the loading area, and the first opening is convenient for removal of the circuit board from the locating blocks.

7. The lens module testing device of claim 4, further comprising four bolts, wherein each of the locating blocks defines a first threaded hole, the circuit board defines four through holes at four corners of the circuit board, each of the through hole spatially corresponds to a respective one of the first threaded holes, the circuit board is supported by the four locating blocks, with each of the through holes aligning with the respective first threaded hole, and the four bolts are run through the four through holes to threadedly engage with the four first threaded holes.

8. The lens module testing device of claim 4, further comprising two bolts, wherein the first flange and the second flange each define a second threaded hole, the shell defines two locating through holes each spatially corresponding to one of the second threaded holes, the connection assembly is supported by the first flange and the second flange, with each of the second threaded holes aligning with a respective one of the locating through holes, and the two bolts are run through the two locating through holes to threadedly engage with the second threaded holes.

9. The lens module testing device of claim 8, wherein a total height of the locating blocks and the circuit board is substantially equal to a height of the first flange, the second flange, the third flange or the fourth flange, along a direction perpendicular to the supporting surface.

10. The lens module testing device of claim 8, wherein the first flange and the second flange each define a second opening, both the two second openings communicate with the slide area.

11. The lens module testing device of claim 2, wherein the slide area comprises a first slide area and a second slide area, the first slide area is adjacent to the loading area, the second slide area is positioned away from the loading area and adjacent to the fourth side surface, a height of the second slide area gradually reduces along a direction from the fourth side surface toward the first slide area, and the second slide area is a slope relative to the first sliding area.

12. The lens module testing device of claim 1, wherein the support assembly comprises a support substrate and a cover covering on the support substrate, the support assembly is slidably positioned on the base in the slide area, the support substrate comprises a first side wall and a second side wall facing away from the first side wall, and each of the first side wall and the second side wall forms a number of fixed seats for loading the lens modules.

* * * * *